(12) United States Patent
Aitken-Christie et al.

(10) Patent No.: US 6,417,001 B2
(45) Date of Patent: *Jul. 9, 2002

(54) EMBRYOGENESIS PROCESS FOR INITIATION

(75) Inventors: Jennifer Aitken-Christie; Bryan Donald Parkes, both of Rotorua (NZ)

(73) Assignee: Carter Holt Harvey Limited, Manukau (NZ)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/952,525

(22) PCT Filed: May 24, 1996

(86) PCT No.: PCT/NZ96/00049

§ 371 (c)(1),
(2), (4) Date: Jan. 30, 1998

(87) PCT Pub. No.: WO97/37046

PCT Pub. Date: Nov. 28, 1996

(30) Foreign Application Priority Data

May 25, 1995 (NZ) ................................. 272211
Jun. 15, 1995 (NZ) ................................. 272635

(51) Int. Cl.⁷ ................................. C12N 5/00
(52) U.S. Cl. ................. 435/422; 435/430; 435/430.1; 435/431
(58) Field of Search ................. 435/422, 430, 435/430.1, 431

(56) References Cited

U.S. PATENT DOCUMENTS

| | | | |
|---|---|---|---|
| 4,957,866 A | 9/1990 | Gupta et al. | |
| 5,034,326 A | 7/1991 | Pullman et al. | |
| 5,036,007 A | 7/1991 | Gupta et al. | |
| 5,041,382 A | 8/1991 | Gupta et al. | |
| 5,294,549 A | 3/1994 | Pullman et al. | |
| 5,413,930 A | 5/1995 | Becwar et al. | |
| 5,677,185 A | 10/1997 | Handley | ..................... 435/422 |

FOREIGN PATENT DOCUMENTS

| | | |
|---|---|---|
| AU | 60707/94 | 10/1994 |
| WO | WO87/02701 | 5/1987 |
| WO | WO93/19585 | 10/1993 |
| WO | WO95/14373 | 6/1995 |
| ZA | 934807 | 7/1993 |

*Primary Examiner*—Leon B. Lankford, Jr.
(74) *Attorney, Agent, or Firm*—Jacobson Holman, PLLC

(57) ABSTRACT

The present invention is a method of producing mature somatic conifer embryos at a higher yield. Explants of immature embryos are placed on or in an initiation medium or on a nurse culture which is on or in the initiation medium. Over a period of time, initiation takes place and the initiated embryos are ultimately matured on an appropriate maturation medium. The initiation medium and the maturation medium may be the same or different but the initiation medium must contain at least ABA and at least one amino acid or at least one amino acid and no ABA. The maturation medium must contain ABA and at least one amino acid. Advantages of the present invention include ensuring greater efficiency in both initiation and maturation of any initiated embryogenic tissue.

25 Claims, 3 Drawing Sheets

FIG. 5

Figure 1:
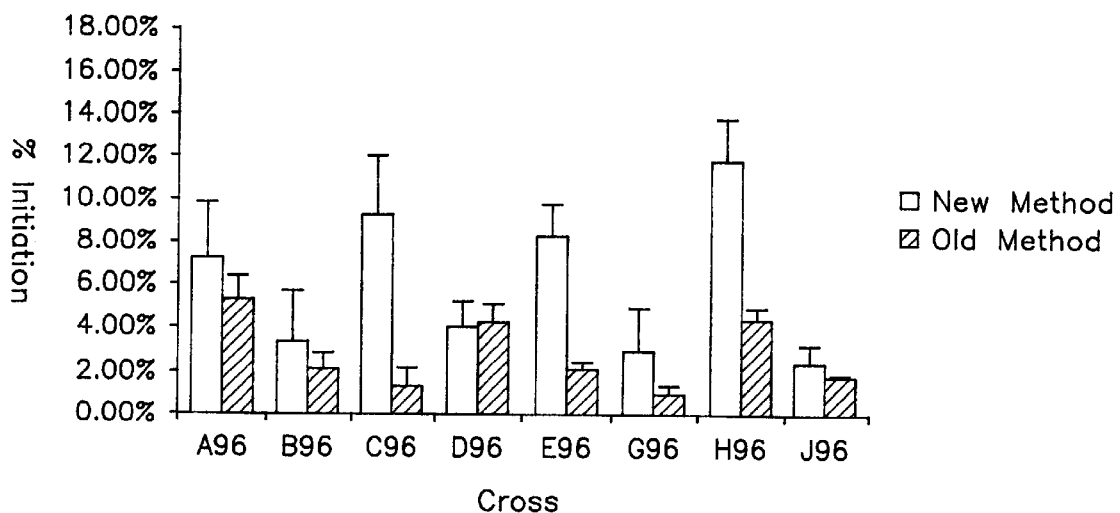

| Meda Code | ABA | Amino Acids | Cross No. | No. of Explants | % Initiation |
|---|---|---|---|---|---|
| 34 | ✓ | ✓ | D96 | 6 | 0 |
|  |  |  | E96 | 42 | 71.4 |
|  |  |  | G96 | 42 | 28.2 |
|  |  |  | J96 | 12 | 25.0 |
|  |  |  | mean | 102 | 40.2 |
| 91 |  | ✓ | D96 | 6 | 16.7 |
|  |  |  | E96 | 42 | 78.8 |
|  |  |  | G96 | 25 | 12.0 |
|  |  |  | J96 | 12 | 0 |
|  |  |  | mean | 85 | 43.5 |
| 92 | ✓ |  | D96 | 4 | 25.0 |
|  |  |  | E96 | 42 | 31.0 |
|  |  |  | G96 | 36 | 2.8 |
|  |  |  | J96 | 12 | 8.3 |
|  |  |  | mean | 94 | 17.0 |
| 93 |  |  | D96 | 0 |  |
|  |  |  | E96 | 42 | 16.7 |
|  |  |  | G96 | 36 | 8.3 |
|  |  |  | J96 | 12 | 0 |
|  |  |  | mean | 90 | 11.1 |

EMBRYOGENESIS PROCESS FOR INITIATION

The present invention relates to an improved conifer or other woody species embryogenesis process for initiation and maturation.

The initiation and maturation of embryogenic tissue and somatic embryos respectively has hitherto been part of a stagewise process from which explant to embryogenic tissue through to germination of somatic embryos and growth of somatic seedlings in the field has involved the 8 stages referred to hereinafter.

1. Initiation of embryogenic tissue
2. Maintenance of embryogenic tissue
3. Development of embryogenic tissue
4. Maturation of somatic embryos
5. Starvation and storage of somatic embryos (see New Zealand Patent Specification No. 272210)
6. Germination of somatic embryos
7. Growth of somatic seedling in greenhouse
8. Growth of somatic seedlings in field Protocols for somatic embryogenesis for conifers typically involve several stages from initiation of embryogenic tissue through to somatic embryo maturation and germination. Patents providing background as to the use of embryogenesis to create somatic embryos include WO95/14373, U.S. Pat. No. 5036007, U.S. Pat. No. 5,034,326, U.S. Pat. No. 5,041,382, U.S. Pat. No. 4,957,866, AU 37150/93, U.S. Pat. No. 5,294,549, South Africa 93/4807, and U.S. (CIP) Ser. No. 08/219879 (unpublished).

For initiation of conifer embryogenic cell lines whole gametophytes containing immature fertilised embryos or dissected immature fertilised embryos are used as explants. Explants are placed on several different "initiation media" to initiate embryogenic tissue either with or without growth regulators. The average percentage initiation over an entire seasonal initiation for radiata pine using whole gametophytes as explants has varied from 5–10%. The best percentage initiation has varied from 6–34% for the best developmental window of sampling the explants from each seedlot. An initiated cell line is defined as an established and maintained cell line.

For maturation of conifer somatic embryos, initiated embryogenic cell lines are placed onto several media to maintain and develop the embryogenic tissue and multiply the number of embryo initials. Embryogenic tissue is then generally placed on a "maturation medium" to encourage the tissue to form mature embryos. Typically this maturation media contains abscisic acid (ABA). The percentage of initiated cell lines that are able to continue growth and form mature somatic embryos is typically 1–10%. Higher percentages of up to 25% have been obtained when a selection of 20–25% of the maintained embryogenic cell lines are placed on maturation media, i.e.; not all cell lines initiated are subsequently suitable for placement on maturation media.

The percentage of cell lines that are currently initiated using previously patented or published protocols is too low for adequate clonal representation within a family or cross and genetic diversity is not maintained satisfactorily.

Furthermore, from the embryogenic cell lines initiated the representation of clones forming mature embryos within a family is further reduced.

It is desirable from the perspectives of clonal testing, genetic diversity, process efficiency and cost effectiveness to have at least 50% initiation of clonal embryogenic cell lines and at least 30% formation of mature somatic embryos from those initiated embryogenic cell lines.

The present invention can achieve or at least approach this.

The present invention relates to various procedures and related methods and includes an embryogenic initiation medium which will result in changes to at least stages 1, the prospect of a merging of steps 2 and 3 with each of stages 1 and 4 and additionally potentiates the outcome at maturation step 4 for that embryogenic tissue capable of generating somatic embryos, the present invention therefore providing an increased efficiency over the prior art procedures.

It is to this that the present invention is directed.

In a first aspect the present invention consists in a method of initiating embryogenic tissue from a source of immature embryos of a conifer or other woody species, said method comprising:

placing explants of the immature embryos on and/or in an initiation medium or on a nurse culture itself on or in the initiating medium, and allowing sufficient time for initiation to take place, wherein (i) the initiation medium contains ABA and/or at least one amino acid, or (ii) the initiation medium containing just amino acids.

As used herein "woody species" includes the groups of species Eucalyptus family, Proteaceae, Myrtaceae, Rosaeceae, Punicaceae, etc.

Preferably said conifer immature zygotic embryo explants for the invention include those of *Pinus radiata* (or Monterey pine), hybrids of *Pinus radiata* and genetically modified *Pinus radiata*. This procedure is also applicable to other conifer species, viz, loblolly pine, Douglas fir, spruce species etc. and, of course, hybrids or genetically modified versions thereof.

Reference to "on" and "in" in respect of the media at least contemplates the use of gelled and/or liquid media.

Preferably said explant is not the whole megagametophyte and preferably is the dissected fertilised embryos at the bullet stage and before the pre-cotyledonary stage, 500—(if radiata pine) celled embryo head developmental stage and most probably different called embryo head counts for other species which have different sized and shaped embryos.

Preferably the initiation medium does not contain traditional/conventional plant growth regulators such as auxins and cytokinins (eg; 2, 4-D, IAA, NAA, IBA, BAP, 2-IP, Zeatin, TDZ, etc). Nor preferably is it a medium for initiation with no growth regulators as outlined in South Africa 93/4807. But it does contain ABA and/or one or more amino acids.

Preferably ABA (Abscisic Acid) is present.

Preferably where said initiating medium is also to be used as the maturation medium ABA is present.

In another preferred form Abscisic Acid (ABA) may be absent but at least one amino acid is present. Preferably said amino acid that is present is one or more of the amino acids Arginine, Asparagine. Glutamine, Citrulline, Ornithine, Lysine, Alanine and Proline.

Preferably Glutamine is present.

Preferably at least one of Asparagine and Arginine is also present.

Preferably Glutamine, Asparagine and Arginine are present.

Preferably the initiation medium contains both ABA and at least one of the aforementioned amino acids and optionally several or all of the aforementioned amino acids.

Preferably said initiation medium includes in addition to said ABA and/or said at least one amino acid and other nutrient sources such as, for example, a source of essential macro and micro elements, vitamins, carbohydrates, inositol etc.

Preferably the initiation medium includes inorganic ions in the following ranges in concentration of the more significant ions in a preferred medium

| ION | CONCENTRATION RANGE (mmoles/l) |
|---|---|
| $NO_3$ | 4.27 |
| $NH_4$ | 0.5–6.8 |
| Ca | 0–0.9 |
| Fe | 0–0.15 |
| Na | 0–7 |
| Zn | 0–0.135 |
| Cu | 0–0.05 |
| Mg | 0–3.24 |

Preferably said ion concentrations are

| ION | CONCENTRATION RANGE (mmoles/l) |
|---|---|
| $NO_3$ | about 17.8 |
| $NH_4$ | about 1.96 |
| Ca | about 0.17 |
| Fe | about 0.10 |
| Na | about 3.85 |
| Zn | about 0.09 |
| Cu | about $9.61 \times 10^{-3}$ |
| Mg | about 1.62 |

In another embodiment preferably also present in the medium are the following inorganic ions or the total presence of inorganic ions is as follows

| ION | CONCENTRATION (mmoles/l) |
|---|---|
| $NO_3$ | 17.80 |
| $NH_4$ | 1.96 |
| TOTAL N | 19.76 |
| P | 1.96 |
| K | 14.16 |
| Ca | 0.17 |
| Mg | 1.62 |
| Cl | $3.42 \times 10^{-1}$ |
| Fe | 0.10 |
| S | 1.83 |
| Na | 3.85 |
| B | 0.13 |
| Mn | $1.62 \times 10^{-2}$ |
| Zn | 0.09 |
| Cu | $9.61 \times 10^{-3}$ |
| Mo | $8.27 \times 10^{-4}$ |
| Co | $8.41 \times 10^{-4}$ |
| I | $6.02 \times 10^{-3}$ |

Preferably also included are 5 g/l–50 g/l (w/v) Sucrose (preferably about 30 g/l).

Preferably it also includes 3–8 grams gellan gum per litre (preferably about 5 grams) or other gelling agent (eg; agar or other).

Preferably it also includes 5 mg/l–50 mg/l (w/v) Abscisic acid (ABA) (preferably about 15 mg/l).

Preferably the amino acids are present in the following ranges

| ION | CONCENTRATION RANGE (mg/l) |
|---|---|
| Arginine | 5,00–2,000 |
| Asparagine | 1,000–4,000 |
| Glutamine | 1,000–10,000 |
| Citrulline | 0–50 |
| Ornithine | 0–50 |
| Lysine | 0–50 |
| Alanine | 0–50 |
| Proline | 0–50 |

Preferably arginine is about 700, preferably asparagine is about 2,100 and preferably glutamine is about 7,300.

In another aspect the present invention consists in a method of initiation of embryogenic tissue from a source of immature conifer or other woody species, said method comprising:

placing explants of the immature fertilised embryos (directly or indirectly eg; nurse culture) on and/or in an initiation medium, and allowing sufficient time for the initiation to take place, wherein the initiation medium contains ABA and amino acids, or wherein the initiation medium contains amino acids and no ABA.

Preferably conifers are the source of the explants.

Preferably the sufficient time is of the order of about 4–6 weeks.

Preferably the environment is in a sterile tissue culture vessel in a controlled environment at 15–28° C.

In a further aspect the present invention consists in a method of initiation of embryogenic tissue from a source of immature conifer or other woody species embryos, said method comprising:

placing explants of the immature fertilised embryos (directly or indirectly eg; nurse cells) on and or in an initiation medium, and allowing sufficient time for the initiation to take place, wherein the initiation medium is;

|  | Final Rate per Litre (mg) |
|---|---|
| Potassium Nitrate ($KNO_3$) | 1431 |
| Magnesium Sulphate ($MgSO_4.7H_2O$) | 400 |
| Sodium Nitrate ($NaNO_3$) | 310 |
| Ammonium Dihydrogen Phosphate ($NH_4H_2PO_4$) | 225 |
| Calcium Chloride ($CaCl_2.2H_2O$) | 25 |
| Zinc Sulphate ($ZnSO_4.7H_2O$) | 25 |
| Boric Acid ($H_3BO_3$) | 8.0 |
| Manganese Sulphate ($MnSO_4.H_2O$) | 2.72 |
| Copper Sulphate ($CuSO_4.5H_2O$) | 2.4 |
| Potassium Iodide (KI) | 1.0 |
| Cobalt Chloride ($CoCl_2.6H_2O$) | 0.2 |
| Molybdic Acid ($Na_2MoO_4.2H_2O$) | 0.2 |
| EDTA - Disodium Salt | 40 |
| Iron Sulphate $7H_2O$ | 30 |
| Nicotinic Acid | 5.0 |
| Thiamine HCl | 5.0 |
| Pyridoxine | 0.5 |
| Inositol | 1000 |
| Arginine | 700 |

-continued

| | Final Rate per Litre (mg) |
|---|---|
| Asparagine | 2100 |
| Glutamine | 7300 |
| Citrulline | 3.95 |
| Ornithine | 3.80 |
| Lysine | 2.75 |
| Alanine | 2.0 |
| Proline | 1.75 |
| Abscisic Acid | 5 to 50 |
| Sucrose | 5,000 to 50,000 |
| Gelling Agent (GELRITE ®) | 3,000 to 8,000 |

Preferably the sucrose is about 30,000, the gelling agent is GELRITE® about 4,500, and the abscisic acid is about 15.

In this respect reader is referred to South African Patent Specification No. SA 93/4807 where media is used for maturation only. The present invention recognises the usefulness and advantages of a media (not necessarily including ABA) for initiation and also (when preferably including ABA) for maturation.

In a further aspect the invention is a method of producing mature somatic embryos comprising the steps (1) placing explants of the immature embryos on and/or in an initiation medium or on a nurse culture itself on or in the initiation medium, (2) allowing the initiation to take place, (3) (whether after optional storage and maintenance or not) maturing the initiated embryos on an appropriate maturation medium, and wherein (a) the initiation and maturation medium may be the same or different, and wherein (b) (i) at least the initiating medium contains ABA and at least one amino acid, or (b) (ii) at least the initiating medium contains at least one amino acid and no ABA.

Preferably said at least one amino acid is selected from the group Arginine, Asparagine, Glutamine, Citrulline, Ornithine, Lysine, Alanine and Proline.

Preferably the maturation medium contains ABA and at least one amino acid.

The invention also consists in embryos thus matured.

In still a further aspect the present invention consists in an initiation and/or maturation media for embryogenic tissue. said medium comprising in addition to a presence of ABA and at least one amino acid, inorganic ions in the following ranges in concentration of the more significant ions in a preferred medium.

| ION | CONCENTRATION RANGE (mmoles/l) |
|---|---|
| $NO_3$ | 4–27 |
| $NH_4$ | 0.5–6.8 |
| Ca | 0.01–0.9 |
| Fe | 0.025–0.15 |
| Na | 0.5–7 |
| Zn | 0.023–0.135 |
| Cu | $6 \times 10^{-4}$–$5 \times 10^{-2}$ |
| Mg | 0.405–3.24 |

Preferably said ion concentrations are

| ION | CONCENTRATION RANGE (mmoles/l) |
|---|---|
| $NO_3$ | about 17.8 |
| $NH_4$ | about 1.96 |
| Ca | about 0.17 |
| Fe | about 0.10 |
| Na | about 3.85 |
| Zn | about 0.09 |
| Cu | about $9.61 \times 10^{-3}$ |
| Mg | about 1.62 |

Preferably said ion concentrations are as follows

| ION | CONCENTRATION (mmoles/l) |
|---|---|
| $NO_3$ | 17.80 |
| $NH_4$ | 1.96 |
| TOTAL N | 19.76 |
| P | 1.96 |
| K | 14.16 |
| Ca | 0.17 |
| Mg | 1.62 |
| Cl | $3.42 \times 10^{-1}$ |
| Fe | 0.10 |
| S | 1.83 |
| Na | 3.85 |
| B | 0.13 |
| Mn | $1.62 \times 10^{-2}$ |
| Zn | 0.09 |
| Cu | $9.61 \times 10^{-3}$ |
| Mo | $8.27 \times 10^{-4}$ |
| Co | $8.41 \times 10^{-4}$ |
| I | $6.02 \times 10^{-3}$ |

Preferably 5 g/l–50 g/l )w/v) Sucrose is also present (preferably about 30g/l).

Preferably 3–8 grams gellan gum per litre (preferably about 4.5 grams) or other gelling agent is also present.

Preferably it also includes 5 mg/l–50 mg/l (w/v) Abscisic acid (ABA) (preferably about 15 mg/l).

Preferably the amino acids are present in the following ranges

| ION | CONCENTRATION RANGE (mg/l) |
|---|---|
| Arginine | 500–2,000 |
| Asparagine | 1,000–4,000 |
| Glutamine | 1,000–10,000 |
| Citrulline | 0–50 |
| Ornithine | 0–50 |
| Lysine | 0–50 |
| Alanine | 0–50 |
| Proline | 0–50 |

Preferably arginine is about 700, preferably asparagine is about 2,100 and preferably glutamine is about 7,300.

In yet a further aspect the present invention consists in and/or an initiation and maturation media for embryogenic tissue, said medium comprising;

| | Final Rate per Litre (mg) |
|---|---|
| Potassium Nitrate (KNO₃) | 1431 |
| Magnesium Sulphate (MgSO₄.7H₂O) | 400 |
| Sodium Nitrate (NaNO₃) | 310 |
| Ammonium Dihydrogen Phosphate (NH₄H₂PO₄) | 225 |
| Calcium Chloride (CaCl₂.2H₂O) | 25 |
| Zinc Sulphate (ZnSO₄.7H₂O) | 25 |
| Boric Acid (H₃BO₃) | 8.0 |
| Manganese Sulphate (MnSO₄.H₂O) | 2.72 |
| Copper Sulphate (CuSO₄.5H₂O) | 2.4 |
| Potassium Iodide (KI) | 1.0 |
| Cobalt Chloride (CoCl₂.6H₂O) | 0.2 |
| Molybdic Acid (Na₂MoO₄.2H₂O) | 0.2 |
| EDTA - Disodium Salt | 40 |
| Iron Sulphate 7H₂O | 30 |
| Nicotinic Acid | 5.0 |
| Thiamine HCl | 5.0 |
| Pyridoxine | 0.5 |
| Inositol | 1000 |
| Arginine | 700 |
| Asparagine | 2100 |
| Glutamine | 7300 |
| Citrulline | 3.95 |
| Ornithine | 3.80 |
| Lysine | 2.75 |
| Alanine | 2.0 |
| Proline | 1.75 |
| Abscisic Acid | 5 to 50 |
| Sucrose | 5,000 to 50,000 |
| Gelling Agent (GELRITE ®) | 3,000 to 8,000 |

Preferably the sucrose is about 30,000, the gelling agent is GELRITE® about 4,500, and the abscisic acid is about 15.

In yet a further aspect the present invention consists in an initiation embryogenic medium that is also effective as a maturation medium for initiated and maintained embryogenic tissue resulting from the initiation.

In still a further aspect the present invention consists in a method of increasing the efficiency of maturation of somatic embryos which comprises initiating and maturing the embryogenic tissue on a (preferably substantially common) medium which either (a) contains ABA and amino acids, (c) is of a composition substantially as follows;

| | Final Rate per Litre (mg) |
|---|---|
| Potassium Nitrate (KNO₃) | 1431 |
| Magnesium Sulphate (MgSO₄.7H₂O) | 400 |
| Sodium Nitrate (NaNO₃) | 310 |
| Ammonium Dihydrogen Phosphate (NH₄H₂PO₄) | 225 |
| Calcium Chloride (CaCl₂.2H₂O) | 25 |
| Zinc Sulphate (ZnSO₄.7H₂O) | 25 |
| Boric Acid (H₃BO₃) | 8.0 |
| Manganese Sulphate (MnSO₄.H₂O) | 2.72 |
| Copper Sulphate (CuSO₄.5H₂O) | 2.4 |
| Potassium Iodide (KI) | 1.0 |
| Cobalt Chloride (COCl₂.6H₂O) | 0.2 |
| Molybdic Acid (Na₂MoO₄.2H₂O) | 0.2 |
| EDTA - Disodium Salt | 40 |
| Iron Sulphate 7H₂O | 30 |
| Nicotinic Acid | 5.0 |
| Thiamine HCl | 5.0 |
| Pyridoxine | 0.5 |
| Inositol | 1000 |
| Arginine | 700 |
| Asparagine | 2100 |
| Glutamine | 7300 |
| Citrulline | 3.95 |
| Ornithine | 3.80 |
| Lysine | 2.75 |
| Alanine | 2.0 |
| Proline | 1.75 |
| Abscisic Acid | 5 to 50 |
| Sucrose | 20,000 to 40,000 |
| Gelling Agent (GELRITE ®) | 2,500 to 8,000 |

Preferably the sucrose is about 30,000, the gelling agent is GELRITE® and is about 4,500, and the abscisic acid is about 15.

Preferably the efficiency is a potentiated increase in the efficiency in that the use of the initiation medium as set out in (c) or containing ABA and amino acids or just amino acids increases the percentage of cell lines produced at initiation of the embryogenic tissue. (FIGS. 1–5). The cell lines initiated by the invention that go on to produce mature somatic embryos is also increased.

The present invention encompasses in the preparation of somatic embryos (particularly of conifers) a merged yet still sequential initiation and maturation procedure using a common or substantially common medium.

The present invention also envisages a procedure of generating mature somatic embryos which comprises:

initiation of embryogenic tissue from a source of immature conifer or other woody species embryos by a procedure of the present invention previously defined, and maturing at least some of the embryogenic tissue to mature somatic embryos on the same medium but removing some of the initiated embryogenic tissue from the medium for bulking up and/or maintenance on a different media or for long term storage by cryo preservation before proceeding with additional maturation for producing much larger numbers of mature somatic embryos on the same or similar medium.

In a further aspect the present invention consists in mature embryos yielded by a method in accordance with the present invention and/or the use of an initiation and/or maturing media as previously set forth.

In yet a further aspect the present invention consists in a harvested product of a conifer or other woody species where the seed and/or seedling has resulted from the use of a method of the present invention and/or an initiation and/or maturing media as previously set forth.

In still a further aspect the present invention consists in wood, wood chips or cellulosic fibre derived from such a harvested product.

Indeed in prior art procedures the stages are as set out below.

1. Initiation of embryogenic tissue
2. Maintenance of embryogenic tissue (optional cryopreservation)
3. Development of embryogenic tissue
4. Maturation of somatic embryos
5. Starvation and storage of somatic embryos (NZ Patent Appi. No. 272210)
6. Germination of somatic embryos
7. Growth of somatic seedling in greenhouse
8. Growth of somatic seedlings in field With the adoption of the present invention, initiation and maturation using the same medium, steps 1 to 4 of such a prior art procedure merge into a combined initiation and maturation stage, the duration of which is approximately 8–12 weeks.

1. Initiation and growth of embryogenic tissue (with optional cryopreservation) 1a.

(optional)Maintenance (with [optional] Cryopreservation)optional Development

2. Maturation of somatic embryos
3. Starvation and storage of somatic embryos (preferably as in New Zealand Patent Specification No. 272210)
4. Germination of somatic embryos
5. Growth of somatic seedling in greenhouse
6. Growth of somatic seedlings in field Somatic embryos produced by this invention can be used in the performance of the invention of our New Zealand Patent Specification No. 272210.

The methods and media of the present invention will now be described with particular reference to *Pinus radiata* as New Zealand's predominant exotic conifer species.

For initiation, whole megagametophyte are not used because of the uncertainty of whether a seed is fertilised or not. If not fertilised, no useful embryogenic tissue is formed.

Dissected fertilised embryos at the bullet stage and before the pre-cotyledonary stage, about 500–1000 called embryo head developmental stage. Other stages of development may be appropriate for other woody species, depending on the size and morphology of fertilised embryos.

Dissected embryos can be placed directly onto the initiation medium or onto a nurse culture. Vigorous growth of embryogenic tissue results.

Initiation media in at least some preferred forms for *Pinus radiata* did not contain traditional/conventional plant growth regulators such as auxins and cytokinins (die; 2, 4-D, IAA, NAA, IBA and BAP, 2-IP, Zeatin, TDZ etc). The media of the present invention does contain ABA and/or some or all amino acids.

Typically initiation obtained with this method and of those initiated typically mature. These results have been shown over a range of eight genetically different families of *Pinus radiata*.

The performance of the present invention will now be described with particular reference to the accompanying drawings against procedures also for *Pinus radiata* as disclosed in South African Patent No. 93/4807.

In the accompanying drawings

Figure 2:
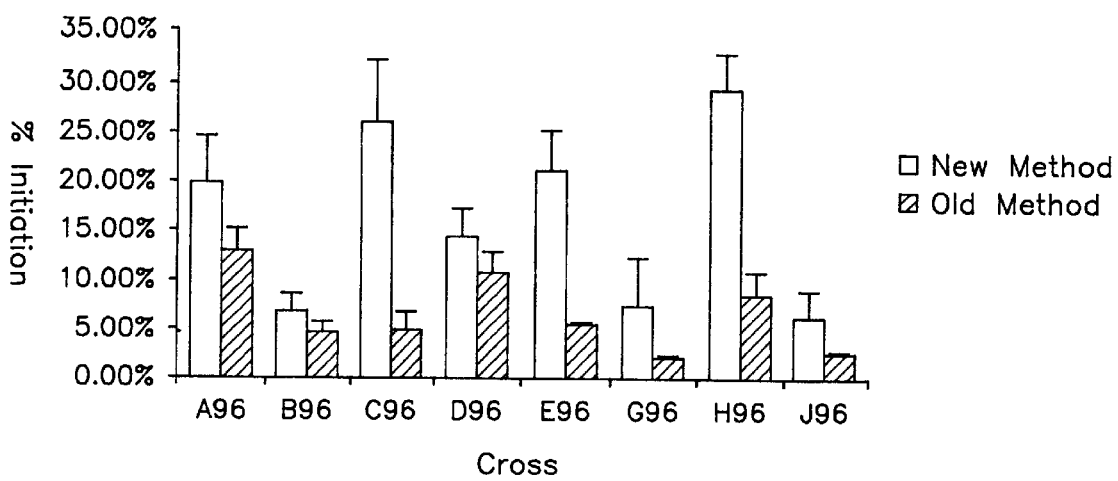
Figure 3:
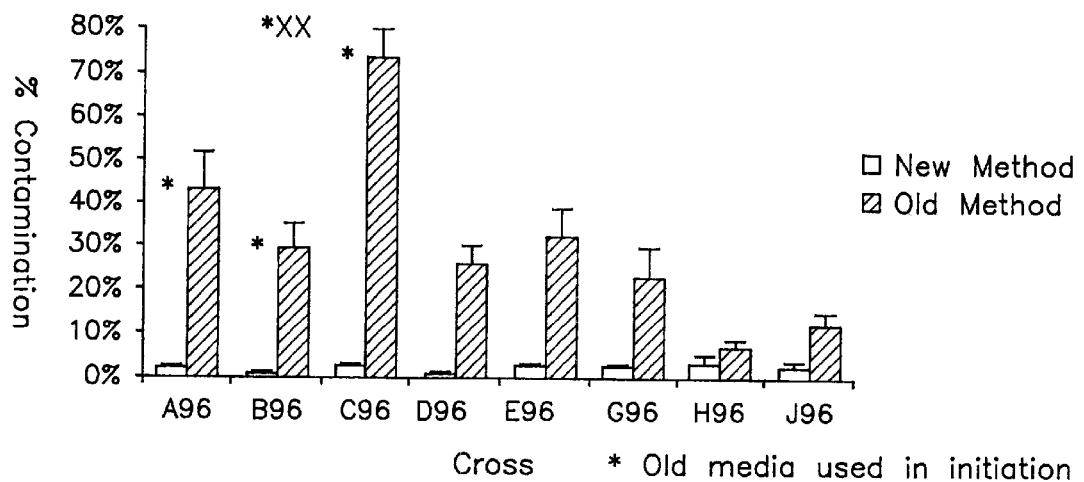
Figure 4:
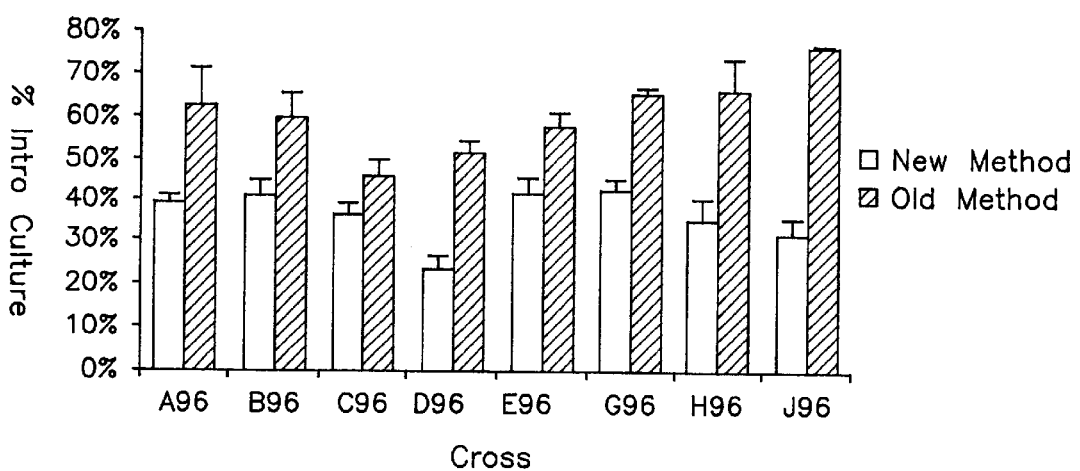

FIG. 1 is a comparison of initiation efficiencies relative to the total seeds extracted between the new method (that of the present invention) and the old method (that of South African Patent No. 93/4807), FIG. 2 is a comparison of initiation efficiencies relative to the number of surviving explants again comparing the new method and the old method, FIG. 3 is a comparison of contamination methods obtained by each initiation method;

FIG. 4 is a comparison of explants into culture as a measure of screening ability; and FIG. 5 shows initiation results for various media types.

Statistical analysis (standard error of the mean) was carried out for all data in FIGS. 1 to 4.

Efficiency of initiation for radiata pine was assessed by two methods, one comparing the efficiency of the two methods relative to total seeds that were extracted from the cones and the other relative to the number of explants that survived being placed into culture. The "new" method is that described in the present invention for the initiation stage only. The "old" method and medium is that described in South African Patent No. 93/4807. Initiation for the purposes of FIGS. 1 and 2 is classified as embryogenic tissue which has grown well enough to be classified as an embryogenic cell-line. Comparison of the two methods was only possible with crosses A96, B96, C96, D96, E96, G96, H96 and J96 initiated in late 1995/early 1996.

The total number of seeds tested for the old method was 16,927 for the purpose of FIG. 1 and for the new was 28,414. For the purpose of FIG. 2 the total number of surviving explants was 7,737 for the old and 9,974 for the new methods.

FIG. 1 shows the difference in initiation efficiency between the two methods relative to staring seed counts. This shows that the new method has, on average, a significantly high efficiency in forming embryogenic cell lines.

The overall percentage initiation with the new method was 9.48% compared with 1.61% for the old method. At the individual cross level the best method was not always the new method, when calculated relative to starting seed counts, as only crosses C96, E96 and H96 were significantly higher in initiation efficiency. This is thought to be related to other factors inherent to the cone (eg. stage of development, felicitation efficiency) and to genetic factors.

FIG. 2, which is a comparison of initiation efficiency relative to the number of surviving explants, shows a similar trend with the old method still showing a lower initiation efficiency. The overall average percentage initiation with the new method was 15.99% compared with 5.99% for the old method.

Embryogenic tissue of *Pinus tamed, Pinus pilaster, Pinus torrent* and *Agates australis* has been successfully initiated using the same method and media outlined in respect to the present invention.

The medium of or used by the methods of the present invention is believed optimal for *Pinus radiata* species for both initiation and maturation but nevertheless has a utility in relation to conifers and woody species in general, at least in respect of initiation, although for some species maintenance in a healthy state may cause difficulty with a common initiation/maturation medium. The *Pinus radiata* species maintained, in the common (preferred) initiation/maturation media, a healthy state for significant periods and tissue of *Pinus pinaster* and *Agates australis* could be proliferated and maintained in a healthy state for at least four months. Explants for the other species were selected at a similar stage of development as radiata pine, for initiation whereby the size and morphology of embryos differed.

Contamination levels obtained from the two initiation methods (FIG. 3) show highly significant differences depending on the initiation method used. This was an unexpected new benefit of the common (substantially common) initiation/maturation media. The old method shows a much higher level of contamination, on average 20 times that of the new method. The overall average percentage contamination with the old method was 30.32% compared with 1.41% for the new method. The extremely high contamination levels of crosses A96 and C96 were associated with the use of old initiation media.

Another way of interpreting the new and old method for initiation is the screening comparisons shown by reference to FIG. 4.

If an initiation method were to allow explants to be screened for initiation efficiency, then the use of media would be reduced, resulting in a cost saving. Comparison of the number of seeds initially extracted from the cone to the number of explants placed into culture can give a measure of the difference in the ability of the two methods to allow screening. The difference between the new and old method (FIG. 4) shows there is an added ability of the new method to allow screening of. explants. On average the new method allows 25% more screening than the old method. The average percentage of explants that could be placed in culture, if a screening procedure was used, using the new method would be 60.23% whereas with the old method would be 35.54%.

The addition or deletion of key components to the new initiation medium in this invention and the effect of these on initiation was evaluated in order to determine which factors were essential. Four treatments were evaluated.
1. Preferred medium containing ABA and amino acids (control).
2. Preferred medium containing amino acids and no ABA.
3. Preferred medium containing ABA and no amino acids.
4. Preferred medium containing no ABA and no amino acids.

FIG. 5 demonstrates that the preferred media are those containing both ABA and amino acids or just amino acids, wherein percentage initiation values were 40.2% and 43.5% respectively. Media without amino acids or with no amino acids and no ABA had significantly lower percentage initiation at 17.0% and 11.1% respectively. Each media was tested with 4 different crosses.

The best percentage initiation of embryogenic cell lines from explants from the top 10 cones for both "new" and "old" methods (out of a total of 552 cones) was 42.91% for the new method and 26.29% for the old method. The initiation efficiency was calculated relative to the number of surviving explants and was statistically analysed (t–test significance<0.003).

Percentage of cell lines forming mature radiata pine somatic embryos using "old" and "new" methods of initiation

|  | No. of Initiated Cell Line | No. of Mature Embryo-Forming Cell Lines | Percentage Maturation Efficiency |
| --- | --- | --- | --- |
| Old* | 3642 | 338 | 9.3 |
| New** | 366 | 114 | 31.1 |

*Pooled data from 2 years (1993/94 and 1994/5 initiations) using "old" method.
**Incomplete data due to experiments ongoing at time of patent completion.

Data on maturation from "old" method in FIGS. 1–5 not available, data shown for "new method above is from 4 crosses.

While in our preferred form of the invention we prefer to use the one medium for both initiation and maturation, the essence of the invention as claimed in respect of initiation and/or maturation media and methods would still be used where a different appropriate nutrient formulation is used for maturation from that used for initiation. Indeed the present invention envisages the use of an initiation or maturation media as claimed or indeed any appropriate initiation or maturation media to which, for maturation purposes at least, ABA and/or anno acids have been added. This is true whether for radiata pine or other conifer or other woody species.

This procedure of the present invention has an advantage of ensuring greater efficiencies of both initiation and maturation of anv initiated embryogenic tissue, the clones being passed through the system to the maturation and beyond to starvation and storage and germination.

What is claimed is:
1. A method for improving initiation of immature embryos comprising the steps of:
   (i) placing explants of immature fertilized embryos of a conifer or other woody species, on or in an initiation medium or, on a nurse culture itself on or in the initiating medium, and
   (ii) allowing initiation of the immature embryos to take place on or in the initiation medium over time, wherein, the initiation medium contains:
      (i) ABA,
      (ii) at least one amino acid, and
   wherein the initiation medium does not contain auxins and does not contain cytokinins.
2. The method of claim 1 wherein the source is a conifer.
3. The method according to claim 2, wherein the source is selected from the group consisting of Pinus radiata, Pinus taeda, Pinus pinaster, Pinus torreyana, and Agathis australis.
4. The method according to claim 2, wherein the source is selected from the group consisting of Pinus radiata, hybrids of Pinus radiata, and genetically modified Pinus radiata.
5. The method of claim 1 wherein said explant is not the whole megagametophyte and is the dissected fertilised embryos at 2 to 500 or more—celled embryo head stage.
6. The method of claim 5 when dissected at about the bullet or 500–1000—celled embryo head stage.
7. The method of claim 1 wherein said amino acid is selected from the group consisting of Arginine, Asparagine, Glutamine, Citrulline, Ornithine, Lysine, Alanine and Proline.
8. The method of claim 1 wherein Glutamine is present.
9. The method of claim 1, wherein at least one of Asparagine and Arginine is present.
10. The method of claim 1 wherein Glutamine, Asparagine and Arginine are present.
11. The method of claim 1 wherein said initiating medium includes in addition to said ABA and said at least one amino acid other nutrient sources.
12. The method of claim 1 wherein the initiation medium includes inorganic ions in the following concentrations

| ION | CONCENTRATION RANGE (mmoles/l) |
| --- | --- |
| $NO_3$ | 4–27 |
| $NH_4$ | 0.5–6.8 |
| Ca | 0–0.9 |
| Fe | 0–0.15 |
| Na | 0–7 |
| Zn | 0–0.135 |
| Cu | 0–0.05 |
| Mg | 0–3.24 |

13. The method of claim 12 wherein said ion concentrations are

| ION | CONCENTRATION RANGE (mmoles/l) |
| --- | --- |
| $NO_3$ | about 17.8 |
| $NH_4$ | about 1.96 |
| Ca | about 0.17 |

-continued

| ION | CONCENTRATION RANGE (mmoles/l) |
|---|---|
| Fe | about 0.10 |
| Na | about 3.85 |
| Zn | about 0.09 |
| Cu | about $9.61 \times 10^{-3}$ |
| Mg | about 1.62 |

14. The method of claim 1 wherein also present in the medium are the following inorganic ions or the total presence of inorganic ions is as follows

| ION | CONCENTRATION (mmoles/l) |
|---|---|
| $NO_3$ | 17.80 |
| $NH_4$ | 1.96 |
| TOTAL N | 19.76 |
| P | 1.96 |
| K | 14.16 |
| Ca | 0.17 |
| Mg | 1.62 |
| Cl | $3.42 \times 10^{-1}$ |
| Fe | 0.10 |
| S | 1.83 |
| Na | 3.85 |
| B | 0.13 |
| Mn | $1.62 \times 10^{-2}$ |
| Zn | 0.09 |
| Cu | $9.61 \times 10^{-3}$ |
| Mo | $8.27 \times 10^{-4}$ |
| Co | $8.41 \times 10^{-4}$ |
| I | $6.02 \times 10^{-3}$ |

15. The method of claim 1 wherein the media contains 5 g/l–50 g/l (w/v) Sucrose.

16. The method of claim 1 wherein the media contains 3–9 grams gellan gum or other gelling agent.

17. The method of claim 1 wherein the amino acids are present in the following ranges

| ION | CONCENTRATION RANGE (mg/l) |
|---|---|
| Arginine | 500–2,000 |
| Asparagine | 1,000–4,000 |
| Glutamine | 1,000–10,000 |
| Citrulline | 0–50 |
| Ornithine | 0–50 |
| Lysine | 0–50 |
| Alanine | 0–50 |
| Proline | 0–50 |

18. The method of claim 1 including allowing at least partial maturation wherein said initiation media is used as the maturation media.

19. The method according to claim 1, wherein the concentration of ABA in the initiation medium is about 15 mg/l.

20. The method according to claim 10, wherein the concentration of Glutamine is about 7,300 mg/l, the concentration of Asparagine is about 2,100 mg/l, and the concentration of Arginine is about 700 mg/l in the initiation medium.

21. The method according to claim 11, wherein the other nutrient sources include a source of essential macro and micro elements, and said source of essential macro and micro elements includes vitamins, carbohydrates, and inositol.

22. A method for improving initiation of imature embryos comprising the steps of:
  (i) placing explants of immature fertilized embryos of a conifer or other woody species, on or in an initiation medium and,
  (ii) allowing initiation of the immature embryos to take place on or in the initiation medium over time,
wherein, the initiation medium is:

| | | Final Rate per Liter (mg) |
|---|---|---|
| Potassium Nitrate | ($KNO_3$) | 1431 |
| Magnesium Sulphate | ($MgSO_4.7H_2O$) | 400 |
| Sodium Nitrate | ($NaNO_3$) | 310 |
| Ammonium Dihydrogen Phosphate | ($NH_4H_2PO_4$) | |
| Calcium Chloride | ($CaCl_2.2H_2O$) | 25 |
| Zinc Sulphate | ($ZnSO_4.7H_2O$) | 25 |
| Boric Acid | ($H_3BO_3$) | 8.0 |
| Manganese Sulphate | ($MnSO_4.H_2O$) | 2.72 |
| Copper Sulphate | ($CuSO_4.5H_2O$) | 2.4 |
| Potassium Iodide | (KI) | 1.0 |
| Cobalt Chloride | ($CoCl_2.6H_2O$) | 0.2 |
| Molybdic Acid | ($Na_2MoO_4.2H_2O$) | 0.2 |
| EDTA-Disodium Salt | | 40 |
| Iron Sulphate $7H_2O$ | | 30 |
| Nicotinic Acid | | 5.0 |
| Thiamine HCl | | 5.0 |
| Pyridoxine | | 0.5 |
| Inositol | | 1000 |
| Arginine | | 700 |
| Asparagine | | 2100 |
| Glutamine | | 7300 |
| Citrulline | | 3.95 |
| Ornithine | | 3.80 |
| Lysine | | 2.75 |
| Alanine | | 2.0 |
| Proline | | 1.75 |
| Abscisic Acid | | 5 to 50 |
| Sucrose | | 5,000 to 50,000 |
| Gelling Agent (GELRITE ®) | | 3,000 to 8,000 |

23. The method according to claim 22, wherein each explant is placed directly in contact with the initiation medium.

24. The method according to claim 22, wherein each explant is placed in contact with a nurse cell, and the nurse cell is placed in contact with the initiation medium.

25. The method according to claim 22, wherein the concentration of ABA in the initiation medium is about 15 mg/l.

* * * * *